United States Patent [19]

Yamamoto et al.

[11] 3,932,637

[45] Jan. 13, 1976

[54] METHODS AND COMPOSITIONS FOR IMPROVING THE FEED INTAKE OF MEAT PRODUCING ANIMALS

[75] Inventors: Hisao Yamamoto, Nishinomiya; Shigeho Inaba, Takarazuka; Mitsuhiro Akatsu, Toyonaka, all of Japan; Clifton A. Baile, Glen Mills; Roger G. Parish, King of Prussia, both of Pa.

[73] Assignees: Sumitomo Chemical Company, Limited, Osaka, Japan; SmithKline Corporation, Philadelphia, Pa.

[22] Filed: July 22, 1974

[21] Appl. No.: 490,813

[52] U.S. Cl. .................................. 424/244; 424/263
[51] Int. Cl.² .................. A61K 31/33; A61K 31/44
[58] Field of Search ...................................... 424/244

[56] References Cited
FOREIGN PATENTS OR APPLICATIONS
1,306,451  2/1973  United Kingdom Primary Examiner—Sam Rosen
Attorney, Agent, or Firm—William H. Edgerton

[57] ABSTRACT

Compositions and methods for inducing polyphagia in immature meat producing animals comprise administering orally or by injection an effective but nontoxic subpharmacodynamic quantity of a 1,4-benzodiazepinone active ingredient whose structure is characterized by an 1-alkyl-sulfonylalkyl moiety. Preferred active ingredients are 1-(ethylsulfonylethyl)-5-(o-halophenyl)-7-halo-1,3-dihydro-2H-1,4-benzodiazepin-2-ones.

14 Claims, No Drawings

METHODS AND COMPOSITIONS FOR IMPROVING THE FEED INTAKE OF MEAT PRODUCING ANIMALS

This invention relates to new methods and compositions for inducing polyphagia or increased feed intake in immature meat producing animals, such as pigs, cattle and sheep, especially in healthy feeder sheep and cattle. The active ingredients of this invention are a series of 1,4-benzodiazepinones substituted by an alkylsulfonylalkyl moiety at position 1. More specifically this method comprises the internal administration to the growing animal preferably orally admixed in the feed but alternatively by injection, as by implant, of a quantity of the 1,4-benzodiazepinone active ingredient which is nontoxic or is not overtly pharmacodynamic but which is sufficient to induce the desired polyphagia in the subject animal. The compositions of this invention are veterinary feed or injectable preparations containing the stated quantities of the 1-alkylsulfonylalkyl-1,4-benzodiazepinone ingredients dispersed uniformly throughout the carrier.

Polyphagia implies an inducement of the animal to eat past its point of satiety thereby increasing the weight of the animal more quickly than normal. This enables the feed lot operator to turn over his pens or lots more quickly. Polyphagia is distinct from more standard means of increasing the feed efficiency of meat-producing animals which involve more efficient use of the animal feed but no increase in the amount ingested by the animal. A full discussion of polyphagia and the methods used for demonstrating polyphagia is contained in Baile et al., *Phys. Rev.*, 54, 160–214 (1974).

Certain 1,4-benzodiazepines lacking the novel 1-moiety have been described to have utility as standard feed additives, German Pat. No. 2,233,117 and U.S. Pat. No. 3,248,223.

The chemicals which are the active ingredients of this invention are members of a narrow class of compounds which have been disclosed among a larger generic class in the art. U.K. Pat. No. 1,309,948 describes these individual chemical ingredients and their use as sedatives, muscle relaxants, hypnotics and anticonvulsants. This reference describes the compounds as therapeutic agents of course implying use in human therapy. Also related compounds are described in U.K. Pat. No. 1,306,451 with essentially the same disclosure of field of utility. In neither of these patents in the prior art are there described application of the ingredients to the animal or veterinary field in any way, and certainly not to the feed lot application described here.

The structures of the preferred 1-alkylsulfonylalkyl-1,4-benzodiazepin-2-ones of this invention are illustrated by the following general formula:

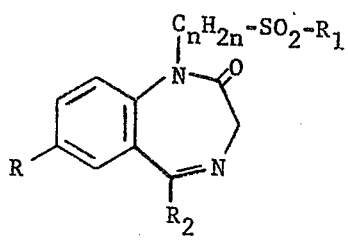

in which:

R is hydrogen, nitro, trifluoromethyl or halo such as iodo, bromo, chloro or fluoro but preferably trifluoromethyl or halo;

$R_1$ is lower alkyl of 1–4 carbon atoms but preferably ethyl;

$R_2$ is phenyl, pyridyl, halophenyl, trifluoromethylphenyl or nitrophenyl but preferably 2-pyridyl, o-chlorophenyl, o-bromophenyl, o-fluorophenyl or o-trifluoromethylphenyl; and $n$ is an integer of from 2–4, preferably 2.

The most advantageous compounds are those in which R is halo and $R_2$ is o-halophenyl with $n = 2$ and $R_1$ is ethyl. Advantageous ingredients are 1-(ethylsulfonylethyl)-5-(o-halophenyl)-7-chloro-2H-1,4-benzodiazepin-2-ones and their stable, nontoxic acid addition salts. The term "halo" implies any of the four elements listed in increasing order of preference; iodo, bromo, fluoro or chloro. The stable acid addition salts of the active ingredients are obtained with acceptable organic and inorganic acids, such as hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid or lactic acid.

The unique portion of the structure of the active ingredients is the alkylsulfonylalkyl moiety at position 1. The compounds having an ethylene group between the sulfonyl group and the nucleus are preferred over their methylene homologs of the prior art since they are somewhat more economical to prepare. Of course, the cost of the chemical ingredient is a very important item when the main utility of the invention involves savings in the production of meat.

Also, the compounds having a terminal ethyl group have unexpectedly been found to have a separation of polyphagic from ataractic or sedative properties. By contrast the compounds having a terminal methyl group at position 1 have been found to be very active sedatives. The ethyl compounds are able to be used for polyphagia over a much wider range of doses without interference by the sedative action of the active ingredients than can the corresponding methyl congeners. This spread in activity makes the compounds easier to use. Of course sedative or ataractic effects work against the desired polyphagia induced by the methods and compositions of this invention. The upper limits of the dose ranges disclosed herein are most often dictated by excess overt pharmacodynamic activity, such as a sedative effect. Therefore the most preferred moiety at position 1 in the chemical structure of the active ingredients is the ethylsulfonylethyl moiety.

The active compounds, such as those of Formula I, can be administered to the immature meat producing animals internally, i.e., either intramuscularly or subcutaneously in the form of sterile veterinary solutions or suspensions for injection or preferably as veterinary pellet implants. More advantageously the compounds are dispersed throughout conventional ruminant animal feed compositions. The feed compositions are then fed to the immature meat producing animals according to methods well-known to the agricultural art. The animals become satiated but continue to feed, thereby increasing weight gain. The amount of the active ingredient in the composition will be a quantity of the 1-alkylsulfonylalkyl-1,4-benzodiazepin-2-one sufficient to induce polyphagia in the satiated immature meat producing animal but not be overtly toxic or pharmacodynamic in the animal subject as noted above. The animal is preferably a ruminant, such as sheep or cattle and most usually is a healthy, immature, growing or fattening animal.

The animal feeds most generally used in conjunction with the method of this invention are either various grain mixtures and/or roughage feeds such as chopped hay commonly fed to growing animals such as pigs, cattle or sheep. The amount of additive used to supplement such feeds will be in a quantity sufficient to increase feed intake and/or improve the feed efficiency of the animal but not to have a toxic or noxious effect, which amount is selected from the broad range of from about 10 mg. to 100 g. per ton of feed, preferably from about 500 mg. to about 20 g. per ton. An average feeder sheep will ingest about 3–4 lbs. of feed daily; an average feeder steer, about 20–25 lbs.

The dose range per sheep daily is a nontoxic but active quantity of active ingredient chosen from the range of from about 20 $\mu$g. to 200 mg., preferably about 1 mg. to 40 mg. The dose range for cattle daily is chosen from about 100 $\mu$g. to 2 g., preferably about 10 mg. to 1 g. The pig dose range is intermediate. The overall broad range of dosage for meat producing animals is within approximately 10 $\mu$g. to 2.5 g. per day, preferably from about 1 mg. to 1 g. per animal per day. For the more active compounds of the class disclosed a preferred range for sheep and cattle is from about 3–150 mg. per animal. The amount of active ingredient used therefore will depend on the weight of the animal, the absolute polyphagic activity of the chemical and the separation of polyphagia from sedation possible with the chemical. Some measure for overfeeding must be present in practicing this invention.

Generally the methods of this invention using parenteral administration comprise injecting by i.v. or i.m. but preferably by implant a polyphagic but nontoxic amount of the active ingredient such as the daily dosage quantities mentioned. Administration may be usually at most once a day but may be varied as polyphagia is desired. Usually the treatment may take place every several days, weeks or even months. The implant forms of the invention might be used only one to three or four times in the growing time of the animal. They might be administered in the ear or intramuscularly in the hind quarter of the animal.

For commercial use, the active ingredients when used in the feed can be readily used as premix formulations in which the chemical is distributed uniformly throughout a measured quantity of a standard animal feed carrier. This premix or concentrate is then mixed with a normal diet for the animal desired. Examples of such carriers are soybean meal, corn oil, ground corn, barley, wheat, mineral mixtures such as vermiculite, diatomaceous earth, corn gluten meal, corn distillers solubles or soyflour. The active ingredient will be in amounts to satisfy the criteria set forth above for whole feed. The active ingredient will usually be present in from about 1–75% by weight of the premix composition. Other forms of feed products are pasture blocks, such as salt or molasses blocks, top dressing preparations or the like.

The animal feed compositions themselves may also contain: roughages such as cellulose, hay, straw, silages, corn stalks, cotton seed hulls, oats, barley and cereal brans; natural oils such as animal fats, fish oils, safflower oil, peanut oil, and cottonseed oil; antioxidants, minerals, vitamins, antibiotics, anthelmintics; and other appropriate medicaments.

Examples of typical prepared animal feed is as follows:

EXAMPLE 1

| Ingredients | Weight per cent |
| --- | --- |
| Mixed hay | 40.0 |
| Ground yellow corn | 45.0 |
| Soybean oil meal | 7.0 |
| Cane molasses | 7.0 |
| Dicalcium phosphate | 0.5 |
| Trace mineral salts | .5 |
| Vitamin A | 300 I.U./lb. |
| Vitamin D | 150 I.U./lb. |
| 1-Ethylsulfonylethyl-5-(o-fluorophenyl)-7-chloro-1,3-dihydro-2H-1,4-benzodiazepin-2-one | 2 mg./lb. |

The method of this invention using feed compositions comprises allowing the growing animal to graze or be fed ad libitum on the supplemented rations or to be fed on a regular schedule.

EXAMPLE 2

| Ingredients | Weight per cent |
| --- | --- |
| 1-Ethylsulfonlyethyl-5-(o-chlorophenyl)-7-chloro-1,3-dihydro-2H-1,4-benzodiazepin-2-one | 500 mg./lb. |
| Calcium sulfate, dihydrate | 20 mg. |
| Gelatin | 4 mg. |
| Magnesium stearate | 1 mg. |
| Talc | 2 mg. |

The active compound and calcium sulfate, dihydrate are mixed and passed through a No. 40 standard mesh screen. The screened mixture is then granulated with hot 15% gelatin solution, screened through a No. 10 mesh screen and dried overnight at 120° F. The granules are again screened through a No. 40 mesh screen and mixed with the magnesium stearate and talc. The granules are compressed into implants using a ⅛ inch flat face punch and die. One implant is administered intramuscularly. Other standard methods of preparing and using implants are described in U.S. Pat. No. 3,428,729 and the references therein as well as in *J. Animal Science*, 27, 1772 (1968) or *J. Biomed. Mater. Res.*, 1, 433 (1967).

Other species of the active ingredients of this invention which may be used as described above and which are prepared using methods referred to above are:

1-($\beta$-methylsulfonylethyl)-5-phenyl-7-trifluoromethyl-1,3-dihydro-2H-1,4-benzodiazepin-2-one, 1-($\beta$-methylsulfonylethyl)-5-phenyl-7-bromo-1,3-dihydro-2H-1,4-benzodiazepin-2-one, 1-($\beta$-methylsulfonylethyl)-5-phenyl-1,3-dihydro-2H-1,4-benzodiazepin-2-one, 1-($\beta$-methylsulfonylethyl-5-(2'-pyridyl)-7-chloro-1,3-dihydro-2H-1,4-benzodiazepin-2-one, 1-($\beta$-methylsulfonylethyl)-5-(o-fluorophenyl)-7-chloro-1,3-dihydro-2H-1,4-benzodiazepin-2-one, 1-($\beta$-methylsulfonylethyl)-5-(2'-pyridyl)-7-bromo-1,3-dihydro-2H-1,4-benzodiazepin-2-one, 1-($\beta$-methylsulfonylethyl)-5-(o-chlorophenyl)-7-chloro-1,3-dihydro-2H-1,4-benzodiazepin-2-one, 1-(β-methylsulfonylethyl)-5-(o-chlorophenyl)-7-nitro-1,3-dihydro-2H-1,4-benzodiazepin-2-one,
1-(β-methylsulfonylethyl)-5-(o-trifluoromethylphenyl)-7-chloro-1,3-dihydro-2H-1,4-benzodiazepin-2-one,
1-(β-ethylsulfonylethyl)-5-phenyl-7-chloro-1,3-dihydro-2H-1,4-benzodiazepin-2-one,
1-(β-ethylsulfonylethyl)-5-phenyl-7-trifluoromethyl-1,3-dihydro-2H-1,4-benzodiazepin-2-one,
1-(β-ethylsulfonylethyl)-5-phenyl-7-bromo-1,3-dihydro-2H-1,4-benzodiazepin-2-one,
1-(β-ethylsulfonylethyl)-5-(2'-pyridyl)-7-bromo-1,3-dihydro-2H-1,4-benzodiazepin-2-one,
1-(β-ethylsulfonylethyl)-5-(o-tolyl)-7-chloro-1,3-dihydro-2H-1,4-benzodiazepin-2-one,
1-(β-ethylsulfonylethyl)-5-(o-chlorophenyl)-7-nitro-1,3-dihydro-2H-1,4-benzodiazepin-2-one,
1-(β-propylsulfonylethyl)-5-phenyl-7-chloro-1,3-dihydro-2H-1,4-benzodiazepin-2-one,
1-(β-propylsulfonylethyl)-5-phenyl-7-nitro-1,3-dihydro-2H-1,4-benzodiazepin-2-one,
1-(β-isopropylsulfonylethyl)-5-(o-chlorophenyl)-7-chloro-1,3-dihydro-2H-1,4-benzodiazepin-2-one,
1-(β-isopropylsulfonylethyl)-5-(o-tolyl)-7-chloro-1,3-dihydro-2H-1,4-benzodiazepin-2-one,
1-(β-isopropylsulfonylethyl)-5-(o-chlorophenyl)-7-nitro-1,3-dihydro-2H-1,4-benzodiazepin-2-one,
1-(γ-methylsulfonylpropyl)-5-phenyl-7-chloro-1,3-dihydro-2H-1,4-benzodiazepin-2-one,
1-(γ-methylsulfonylpropyl)-5-phenyl-7-nitro-1,3-dihydro-2H-1,4-benzodiazepin-2-one,
1-(γ-methylsulfonylpropyl)-5-(o-fluorophenyl)-7-chloro-1,3-dihydro-2H-1,4-benzodiazepin-2-one,
1-(γ-methylsulfonylpropyl)-5-(o-chlorophenyl)-7-chloro-1,3-dihydro-2H-1,4-benzodiazepin-2-one,
1-(γ-ethylsulfonylpropyl)-5-phenyl-7-chloro-1,3-dihydro-2H-1,4-benzodiazepin-2-one,
1-(γ-ethylsulfonylpropyl)-5-phenyl-7-nitro-1,3-dihydro-2H-1,4-benzodiazepin-2-one,
1-(γ-ethylsulfonylpropyl)-5-phenyl-7-trifluoromethyl-1,3-dihydro-2H-1,4-benzodiazepin-2-one,
1-(γ-ethylsulfonylpropyl)-5-phenyl-7-bromo-1,3-dihydro-2H-1,4-benzodiazepin-2-one,
1-(γ-ethylsulfonylpropyl)-5-(2'-pyridyl)-7-chloro-1,3-dihydro-2H-1,4-benzodiazepin-2-one,
1-(γ-ethylsulfonylpropyl)-5-(o-fluorophenyl)-7-chloro-1,3-dihydro-2H-1,4-benzodiazepin-2-one,
1-(γ-ethylsulfonylpropyl)-5-(2'-pyridyl)-7-bromo-1,3-dihydro-2H-1,4-benzodiazepin-2-one,
1-(γ-ethylsulfonylpropyl)-5-(o-chlorophenyl)-7-chloro-1,3-dihydro-2H-1,4-benzodiazepin-2-one,
1-(γ-ethylsulfonylpropyl)-5-(o-trifluoromethylphenyl)-7-chloro-1,3-dihydro-2H-1,4-benzodiazepin-2-one,
1-(β-ethylsulfonylethyl)-5-(o,o'-difluorophenyl)-7-chloro-1,3-dihydro-2H-1,4-benzodiazepin-2-one,
1-(β-ethylsulfonylethyl)-5-(o,o'-dichlorophenyl)-7-chloro-1,3-dihydro-2H-1,4-benzodiazepin-2-one,
1-(β-ethylsulfonylethyl)-5-(o-fluoro-o'-chlorophenyl)-7-chloro-1,3-dihydro-2H-1,4-benzodiazepin-2-one,
1-(β-isopropylsulfonylethyl)-5-(o,o'-dichlorophenyl)-7-chloro-1,3-dihydro-2H-1,4-benzodiazepin-2-one,
1-(β-methylsulfonylethyl)-5-phenyl-7-chloro-1,3-dihydro-2H-1,4-benzodiazepin-2-one.

Other ingredients are prepared by similar methods. Representative active ingredients were given by injections to sheep or cattle in the following procedures:

EFFECTS ON FEED INTAKE OF CHEMICALS INJECTED INTRAVENOUSLY INTO SHEEP

Groups of sheep, fed ad lib, were given fresh feed one hour before injection (this resulted in eating and assured that the sheep were satiated at injection time). Feed was weighed after 30 and 120 min. Feed intakes were compared to an average control intake following injection of carrier.

TABLE I

| Dose (mg./sheep) | No. Animals | Intake (g+SEM) | % Increase[1] |
|---|---|---|---|
| 7-Chloro-1,3-dihydro-1-methylsulfonylethyl-5-phenyl-2H-1,4-benzodiazepin-2-one | | | |
| 0 | 30 | 76±9 | |
| 4 | 8 | 88±23 | 105 |
| 8 | 8 | 118±14 | 157 |
| 16 | 7 | 222±54 | 313 |
| 32 | 8 | 167±32 | 223 |
| 7-Chloro-1,3-dihydro-1-ethylsulfonylethyl-5-phenyl-2H-1,4-benzodiazepin-2-one | | | |
| 0 | 31 | 73±8.3 | |
| 8 | 8 | 55±14 | 79 |
| 16 | 7 | 248±39 | 331 |
| 32 | 8 | 284±35 | 394 |
| 7-Chloro-1,3-dihydro-1-n-propylsulfonylethyl-5-phenyl-2H-1,4-benzodiazepin-2-one | | | |
| 0 | 30 | 72±6.8 | |
| 8 | 8 | 131±24 | 182 |
| 16 | 8 | 113±16 | 159 |
| 32 | 8 | 61±9.9 | 85 |
| 7-Chloro-1,3-dihydro-5-(o-fluorophenyl)-1-methylsulfonylethyl-2H-1,4-benzodiazepin-2-one | | | |
| 0 | 30 | 75±10 | |
| 1 | 8 | 70±21 | 100 |
| 2 | 8 | 123±15 | 164 |
| 4 | 8 | 199±36 | 237 |
| 8 | 8 | 78±25 | 111 |
| 16 | 8 | 404±38 | 539 |
| 32[2] | 8 | 423±79 | 564 |
| 7-Chloro-1,3-dihydro-1-ethylsulfonylethyl-5-(o-fluorophenyl)-2H-1,4-benzodiazepin-2-one | | | |
| 0 | 30 | 89±12 | 0 |
| 1 | 14 | 87±19 | −1 |
| 2 | 8 | 192±40 | 106 |
| 4 | 8 | 223±27 | 140 |
| 16 | 15 | 313±72 | 244 |
| 32 | 8 | 132±56 | 144 |
| 64 | 8 | 121±12 | 44 |

[1] 0 dose is an average of all values used during testing. % increase figure is compared to specific control value used for dose.
[2] Sheep were slightly ataxic and several were bloated.

EFFECTS ON FEED INTAKE OF CHEMICALS INJECTED INTRAVENOUSLY INTO CATTLE

Groups of cattle, fed ad lib, were given fresh feed 1 hour before injection (this resulted in eating and assured that the cattle were satiated at injection time). Feed was weighed after 60 min. Feed intakes were compared to intake following injection of carrier.

TABLE II

| Dose (mg./steer) | No. Animals | Intake (kg+SEM) | % Increase[1] |
|---|---|---|---|
| 7-Chloro-1,3-dihydro-1-ethylsulfonylethyl-5-(o-fluorophenyl)-2H-1,4-benzodiazepin-2-one | | | |
| 0 | 8 | .18±.08 | 0 |
| 5 | 8 | .37±.10 | 106 |
| 10 | 7 | .36±.10 | 100 |
| 20 | 8 | .48±.11 | 167 |
| 40 | 8 | .79±.17 | 339 |

[1] 0 dose is an average of all values used during testing. % increase figure is compared to this average.

EFFECT ON FEED INTAKE OF CHEMICALS ADMINISTERED IN FEED

Eight sheep were fed a basal ration for two days. They were then fed for two days the basal ration in which chemical had been mixed. Intake of feed with drug added was compared to intake of feed with no drug added.

TABLE III

| | | Feed Intake | | | | |
|---|---|---|---|---|---|---|
| | | Pretreatment | Treatment | | | |
| Dose | No. | 2-Day Av. Intake | First Day Intake | % | 2-Day Average Intake | % |
| (mg./-kg feed) | Animals | (g+SEM) | (g+SEM) | Incr. | (g+SEM) | Incr. |
| 7-Chloro-1,3-dihydro-1-ethylsulfonylethyl-5-(o-fluorophenyl)-2H-1,4-benzodiazepin-2-one | | | | | | |
| 2 | 6 | 1394±93 | 1427±108 | 2.3 | 1435±107 | 2.9 |
| 4 | 8 | 1456±45 | 1602±53 | 10.0 | 1568±52 | 7.6 |
| 8 | 8 | 1491±77 | 1734±68 | 16.2 | 1637±68 | 9.7 |
| 16 | 8 | 1436±77 | 1629±101 | 13.3 | 1550±89 | 7.9 |

We claim:

1. The method of inducing increased feed efficiency or feed intake in immature meat producing animals comprising administering to said animals internally in a feed composition or as an implant an effective but nontoxic quantity of a compound or one of its pharmaceutically acceptable non-toxic acid addition salts of the compound having the formula:

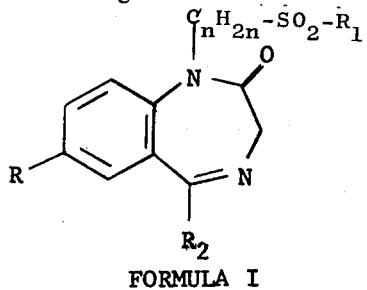

FORMULA I in which:
R is hydrogen, nitro, trifluoromethyl or halo;
$R_1$ is lower alkyl of 1–4 carbon atoms;
$R_2$ is phenyl, 2-pyridyl, o-halophenyl, o-trifluoromethylphenyl or o-nitrophenyl; and
n is an integer of from 2–4.

2. The method of claim 1 in which R is halo or trifluoromethyl, $R_1$ is ethyl, $R_2$ is o-halophenyl or o-trifluoromethylphenyl and n is 2.

3. The method of claim 1 in which R is chloro, $R_1$ is ethyl, $R_2$ is o-halophenyl and n is 2.

4. The method of claim 1 in which R is chloro, $R_1$ is ethyl, $R_2$ is o-chlorophenyl and n is 2.

5. The method of claim 1 in which R is chloro, $R_1$ is ethyl, $R_2$ is o-fluorophenyl and n is 2.

6. The method of claim 1 in which the daily oral dose per animal is chosen from the range of about 1 mg. to 1 g. of the compound.

7. The method of claim 2 in which the daily oral dose per animal is chosen from the range of about 1 mg. to 1 g. of the compound.

8. The method of claim 4 in which the daily oral dose per animal administered in a feed composition is chosen from the range of about 3–150 mg.

9. The method of claim 5 in which the daily dose per animal administered in a feed composition is chosen from the range of about 3–150 mg. per sheep or cattle.

10. A feed composition for meat producing animals having the ability to increase the feed intake or feed efficiency of immature meat producing animals comprising a veterinary feed carrier and as an active ingredient dispersed in said carrier in a quantity sufficient to induce said activity in said animals but not toxic and not overtly pharmacodynamic to said animals a compound of the formula:

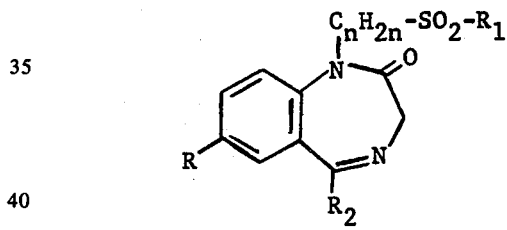

in which:
R is hydrogen, nitro, trifluoromethyl or halo;
$R_1$ is lower alkyl of 1–4 carbon atoms;
$R_2$ is phenyl, 2-pyridyl, o-halophenyl, o-trifluoromethylphenyl or o-nitrophenyl; and
n is an integer of from 2–4.

11. The composition of claim 10 in which the compound is 7-halo-1,3-dihydro-5-(o-halophenyl)-1-ethylsulfonylethyl-2H-1,4-benzodiazepin-2-one within the range of about 3–150 mg. per animal.

12. The composition of claim 11 in which the halos are chloro or fluoro.

13. The composition of claim 11 in which the halo is chloro and the animal is sheep or cattle.

14. The composition of claim 11 in which the compound is 7-chloro-1,3-dihydro-5-(o-fluorophenyl)-1-ethylsulfonylethyl-2H-1,4-benzodiazepin-2-one and the animal is sheep or cattle.

* * * * *